United States Patent [19]

Skubitz et al.

[11] Patent Number: 4,466,441
[45] Date of Patent: Aug. 21, 1984

[54] IN-LINE AND BIFURCATED CARDIAC PACING LEAD CONNECTOR

[75] Inventor: Frank L. Skubitz, Andover, Minn.; James G. Deluhery, Madison, Wis.

[73] Assignee: Medtronic, Inc., Minneapolis, Minn.

[21] Appl. No.: 404,246

[22] Filed: Aug. 2, 1982

[51] Int. Cl.³ ............................................... H61N 1/00
[52] U.S. Cl. ............................ 128/419 P; 128/419 PS
[58] Field of Search ......... 128/419 P, 419 PS, 419 PG

[56] References Cited

U.S. PATENT DOCUMENTS

| 4,105,037 | 8/1978 | Richter et al. | 128/419 P |
| 4,245,642 | 1/1981 | Skubitz et al. | 128/419 P |
| 4,276,882 | 7/1981 | Dickhudt et al. | 128/419 P |

*Primary Examiner*—Edward M. Coven
*Attorney, Agent, or Firm*—Glenn W. Bowen; John L. Rooney; Joseph F. Breimayer

[57] ABSTRACT

A lead connector is disclosed for connecting cardiac pacing leads to a pulse generator through a cable. The lead connector is capable of receiving either in-line or bifurcated leads. The electrodes of the leads need not be of the same diameter due to the construction of a clamping assembly which clamps the lead electrodes to the connector electrodes. The clamping assembly includes a threaded shaft which receives a threaded nut that is retained in a clamping block. The clamping block is constructed so that it may rock relative to the shaft on a domed outer surface of the nut, thereby allowing clamping arms on the clamping block to press against the lead electrodes even if they are of different diameters. A second version of the connector has two clamping blocks and is capable of receiving either a bifurcated lead or an in-line lead, or alternately, both ventricular and atrial leads of either type at the same time.

4 Claims, 9 Drawing Figures

U.S. Patent   Aug. 21, 1984   Sheet 1 of 4   4,466,441
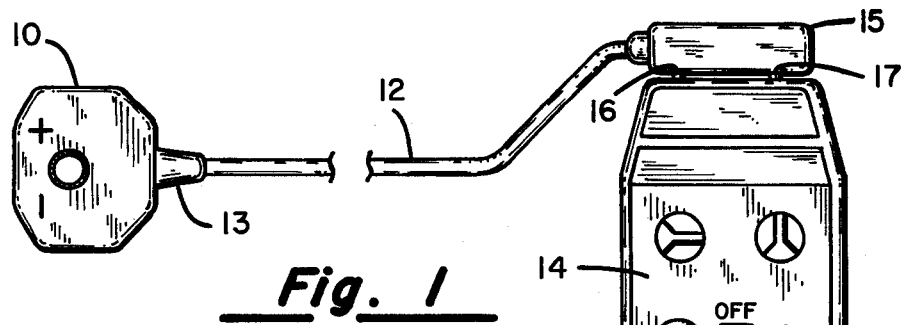
Fig. 1
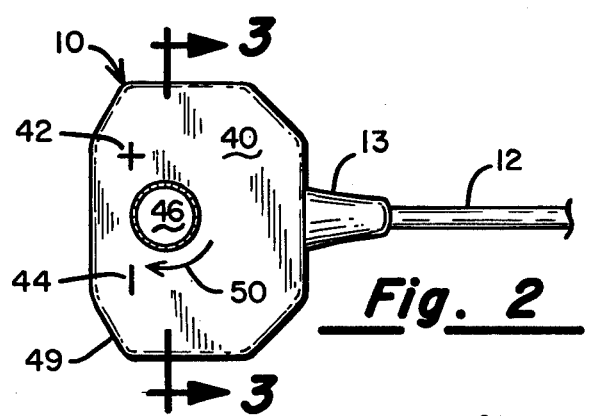
Fig. 2
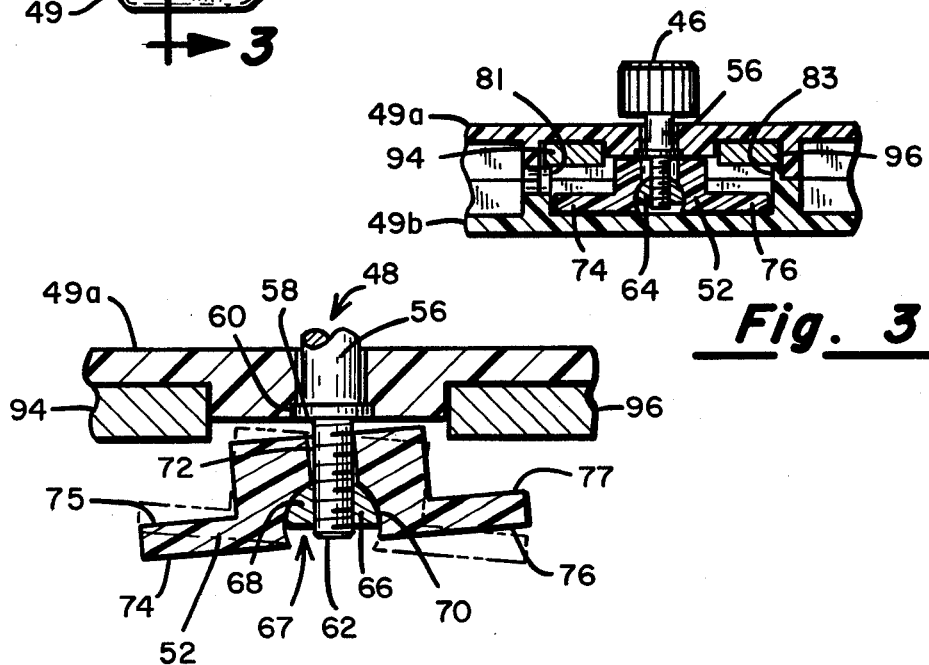
Fig. 3
Fig. 4

IN-LINE AND BIFURCATED CARDIAC PACING LEAD CONNECTOR

BACKGROUND OF THE INVENTION

1. Field of the Invention

The present invention relates generally to lead connectors for easily and quickly interconnecting a temporary pacing lead to a pulse generator.

2. Background of the Prior Art

In the past pulse generators have generally utilized binding post or squeeze connectors for temporary connection which proved to be inadequate for making connection to more advanced temporary pacing leads in order to make connection to an external pacemaker. The need to easily and quickly interconnect the temporary leads to the external pacemaker without complex interconnecting cable or interconnecting structure was met by the lead connector of U.S. Pat. No. 4,245,642 issued Jan. 20, 1981 in the names of Frank Skubitz and Roger L. Funk, which patent is assigned to the assignee of the present invention.

The lead connector of the Skubitz, et al patent was well suited for interconnecting a temporary bipolar lead to two generally U-shaped elongated connector pins which were affixed to the housing of the lead connector. The bipolar lead which was inserted into this lead connector had one electrode area on its end and another electrode area spaced apart from the end, and insulated therefrom, with the entire lead structure being substantially the same diameter. In this manner, the tip electrode contacted one U-shaped permanent connecting pin while the interior spaced apart electrode contacted the other. A spring biased pressure plate was forced down by means of a rotatable thumb screw which operated to deflect the spring and the pressure plate so that it engaged the top of the bipolar lead forcing it down into contact with the two generally U-shaped fixed connecting pins.

This lead connector had a number of desirable features which are desirably retained in the lead connecting device of the present invention. One such feature was that the outer housing of the connector was transparent so that medical personnel, such as cardiologists, could see that the pacing lead was properly inserted and secured within the lead connector. The lead connector was a very simple design thereby minimizing any cause of failure or misuse, and it was reusable. The connector was constructed from readily available materials and the housing was of the plastic injection molded type, formed from polysulfone or similar material. The lead connector was designed so that the lead could be semi-permanently installed for any period of time.

While all of these advantages were present in the lead connector of the Skubitz, et al U.S. Pat. No. 4,245,642 the connector could only be used with in-line type of leads and not bifurcated ones. In addition, the connector was not suited for receiving leads that had electrodes of varying diameters, as is often the case with implantable leads of the in-line variety. The lead connector of the present invention retains all of the above-mentioned advantages of the lead connector of the previous Skubitz, et al patent while making it possible to interconnect not only in-line bipolar leads, but also bifurcated leads and in-line leads of varying electrode diameters.

SUMMARY OF THE INVENTION

A lead connector for connecting pacing leads to a pulse generator is provided which has a housing that has at least one inlet opening for an in-line electrode lead and at least one pair of spaced inlet openings for a bifurcated lead; at least one pair of connector electrodes are secured in the housing and are positioned to contact the electrodes of the leads when they are inserted into the inlet opening; a clamping device is associated with each pair of connector electrodes which include a threaded shaft that has a free end that extends into the housing, a clamping block through which the free end of the threaded shaft protrudes and a securing nut which is threaded onto the free end of the threaded shaft. The securing nut has a curved surface and the clamping block has a mating curved surface for the curved surface of the securing nut which receives the securing nut and prevents it from rotating. The clamping block is constructed so that it may rock to a limited extent relative to the threaded shaft by sliding of its mating curved surface on the curved surface of the securing nut; and the clamping block is driven toward a pair of connector electrodes so as to clamp the inserted lead electrodes between the clamping block and the pair of connector electrodes upon rotation of its threaded shaft in one direction and is driven away from the pair of connector electrodes upon rotation of the threaded shaft in the opposite direction.

DESCRIPTION OF THE DRAWINGS

The invention is described by reference to the drawings in which:

FIG. 1 is a plan view that shows a pacing lead connected between a pulse generator and one embodiment of the lead connector of the present invention;

FIG. 2 is an enlarged plan view of the lead connector of FIG. 1;

FIG. 3 is a cross-sectional view of the lead connector of FIG. 2 taken along the lines 3—3 of FIG. 2;

FIG. 4 is an enlarged partial cross-sectional view of FIG. 3;

TECHNICAL DESCRIPTION OF THE INVENTION

Figure 5:
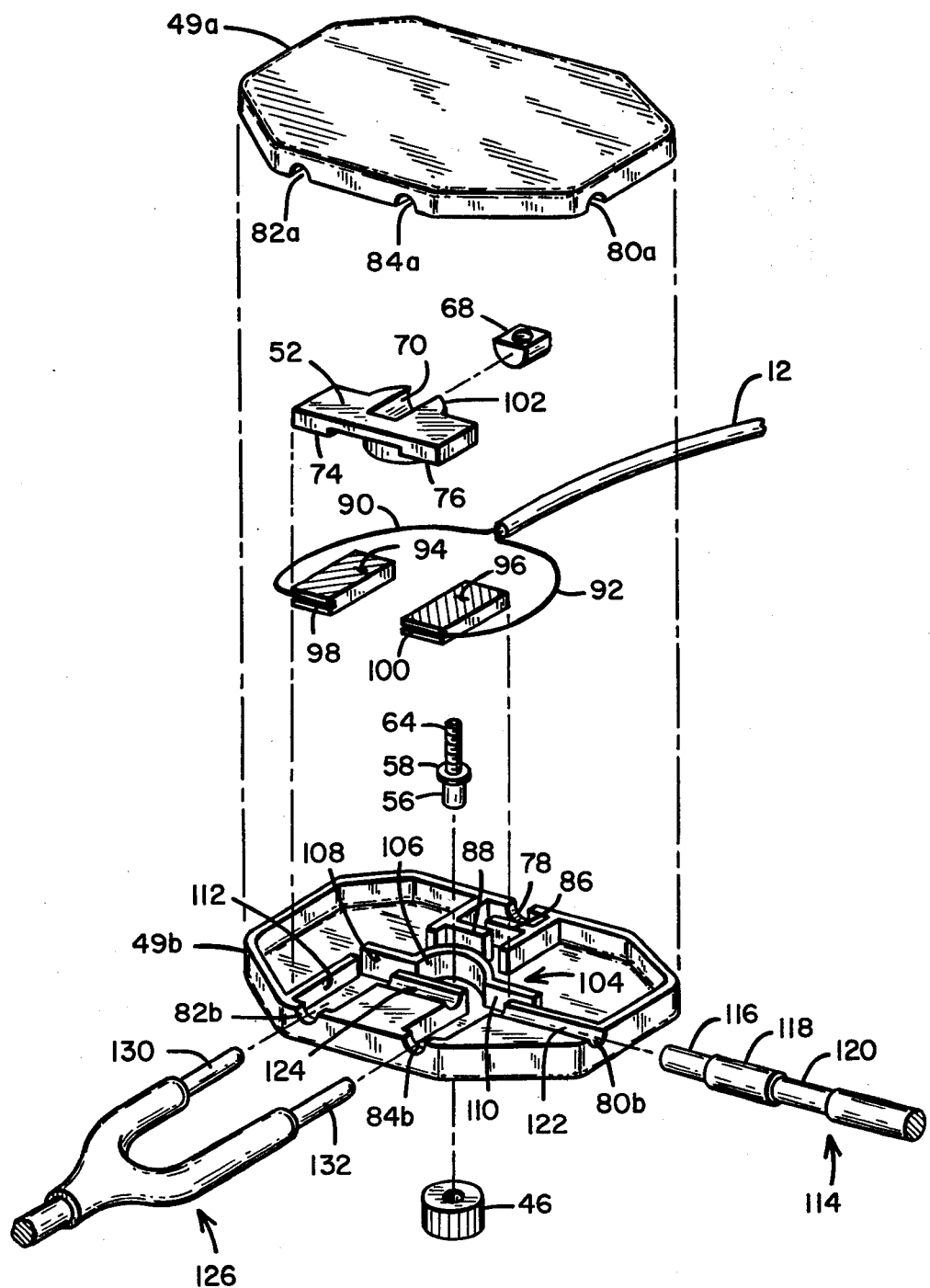
FIG. 5 is an exploded view of a lead connector that corresponds to the lead connector of FIG. 1.

FIG. 1 shows a lead connector 10 constructed in accordance with the present invention which is coupled through a cable 12 to an external pulse generator 14. The prior lead connector of the Skubitz, et al U.S. Pat. No. 4,245,642 was constructed so that the two connecting pins extending through the housing of the connector case would be inserted directly into the external pulse generator so that the connector would be fixed firmly on the top of the generator. It has been found, however, that this limits the usefulness of the device and that it is more desirable for the lead connector to be connected to a cable and then through a separate connector pin 12 to the external pulse generator. It is a variation, however, within the scope of the present invention to mount the lead connector directly on top of the pulse generator as shown in the aforementioned Skubitz et al patent.

FIG. 2 shows a lead connector 10 constructed in accordance with the present invention. The upper surface 40 of the lead connector 10 is marked with a plus mark 42 and a minus mark 44 which indicate the proper polarity of the leads. A clamping knob 46 is secured to a shaft assembly 48 which projects into the interior of the housing 49 which is formed of the upper and lower housing halves 49a, and 49b. When the knob 46 is rotated in the clockwise direction, indicated by the arrow 50 in FIG. 2, a clamping block 52, (shown in FIG. 3), is drawn upwardly so as to clamp on to the electrodes of the leads thereby firmly engaging them with the electrodes in the lead connector.

FIG. 4 is an enlarged view of the clamping block 52 and the shaft assembly 48 of FIG. 3. The shaft assembly 48 has an enlarged cylindrical portion 56 which receives the knob 46. The cylindrical section 56 has an enlarged ring 58 at its lower end which is retained in a groove 60 in the upper housing half 49a to keep the shaft assembly from being removed from the housing. A lower threaded section 62 of the shaft assembly 48 extends into the housing 49.

The threaded section 62 of the shaft assembly 48 is captured by a threaded nut 64 of special construction. The bottom surface 66 is flat while the upper surface 68 is curved, or domed. The nut 64 may be hemispherically shaped, if desired. The clamping block 52 is formed with a recess 67 that has a curved space that generally conforms to the curved surface 68 of the nut. The recess 67 leads to a passageway 72 that surrounds the threaded section 62 and is of the larger diameter than the diameter of the threaded shaft by an amount that allows the clamping block 52 to rock from the dotted line nominally flat position to the full line position as shown in FIG. 4. The surface 70 of the recess 67 thus slides on the upper domed surface 68 of the nut 64 when the clamping block rocks to either side. The dotted line nominally flat position of the clamping block is the position of the block when equal diameter lead electrodes are inserted into the connector and are clamped by the block 52. The full line rocked position of 53 occurs when the clamping block 52 is secured on a lead that has a larger diameter electrode on the left side of the connector, which is clamped between the arm 74 and the connector electrode 94, than on the right side of the connector, which is clamped by the arm 76 and the connector electrode 96.

FIG. 5 is an exploded view of a lead connector that corresponds to the lead connector of FIGS. 1–4 with the only difference being that strain relief for the connecting cable 12 is not provided by the strain relief bushing 13, but instead by an internal housing construction. In this embodiment there are four openings through the housing into the interior of the lead connector. These openings are formed by semi-circular notches on the upper and lower housing halves 49a, 49b. An opening is provided at the rear of the connector by the notch 78 that is formed in the lower housing half 49b and by a matching notch (not shown) that is formed in the upper housing half 49a. This opening receives the cable 12 therein, and strain relief is provided for this cable by allowing it to wind through the strain relief walls 86, 88. The wires 90, 92 of the cable 12 are connected to the electrodes 94, 96 of the lead connector.

The electrodes 94, 96 are secured in the connector by the receipt of tongues (not shown) which are integrally formed in the lower housing half 49b in the grooves 98, 100.

The clamping block 52 has a curved projection 102 formed on it (FIG. 5) and the lower housing half 49b is formed with an integral wall 104 which has a curved section 106 that corresponds in shape generally to the projection 102. The curved wall section 106 thereby prevents the clamping block 52 from rotating when the knob 46 is rotated. The wall 104 has two straight wall sections 108 and 110 on opposite sides of the curved wall section 106. Another straight wall 112 is integrally formed on the lower housing of 49b and runs generally normal to the wall section 108. An opening is formed on the right side of the lead connector, by the semicircular notches 80a, and 80b which may receive an in-line lead, such as the lead 114 which is illustrated in FIG. 5. The lead 114 in FIG. 5 is a bipolar lead which has two uniform diameter electrodes, but the lead could also be a unipolar lead, or a bipolar lead with different diameter electrodes. The lead 114 has a negative electrode tip 116 on it, an insulating ring 118 and a positive electrode 120. When the lead 114 is inserted into the opening formed by the notches 80a, 80b the end of the electrode tip 116 abuts against the wall section 112 thereby locating the lead electrodes 116, 120 adjacent the connector electrodes 94, 96, respectively. If the lead 114 were a unipolar lead only one of the electrodes 116, 120 would be employed.

The lead electrodes 116, 120 are clamped against the connector electrodes 94, 96 respectively when the knob 46 is rotated in the clockwise direction of the arrow 50. This causes the clamping block 52 to be drawn upwardly on the threaded section 62 of the shaft assembly 48, due to the interaction of the threaded section 62 and the nut 64 which is retained in the clamping block. As the clamping block 52 moves toward the connector electrodes it drives the arms 74, 76 upwardly so that the upper surfaces 75, 77 eventually abut against the lead electrodes 116, 120 and lock them in place against the connector electrodes 94, 96. As previously mentioned, the diameter of the lead electrodes does not have to be the same because the clamping block 52 can rock transversely, as shown in FIG. 4. The lead 114 is supported over part of its passageway into the housing of the connector by the channels 122, 124 which are formed on the lower housing half 49b.

Figure 6:
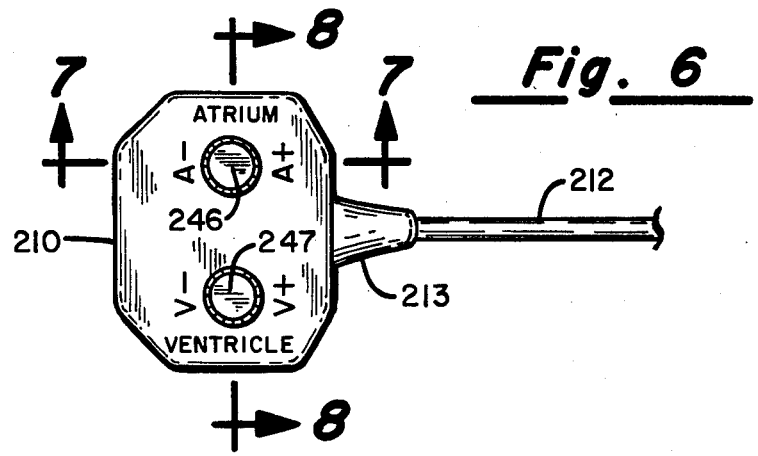
FIG. 6 is a plan view of an alternate lead connector which is capable of receiving both atrial and ventricular pacing leads.
Figure 7:
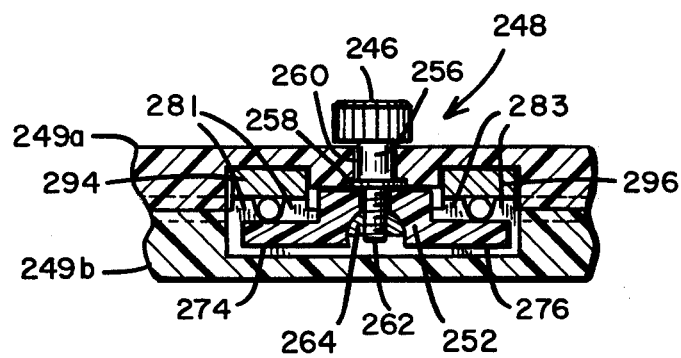
FIG. 7 is a cross-sectional view of the lead connector of FIG. 6 taken along the lines 7—7 of FIG. 6.

With modern cardiac pacing generators it is often desirable to be able to interconnect both atrial and ventricular temporary pacing leads to a pulse generator. The lead connector embodiment of the present invention that is shown in FIGS. 6–9 has this capability. The lead connector 210 is shown in FIG. 6 with a strain relief bushing 213 and an interconnecting cable 212. Two clamping knobs 246 and 247 are shown which are used to provide the clamping. Each of the knobs is used to clamp one of the atrial or ventricle interconnecting leads against corresponding lead electrodes in the connector. The cross-sectional view of FIG. 7 shows the clamping block 252 and the threaded shaft assembly 248 which is associated with the knob 246. In FIG. 7, two equal diameter leads are shown as being clamped into place in this portion of the connector. The construction of the elements as shown in FIG. 7 is substantially identical to those shown in FIG. 3, but the element numbers of FIG. 7 are 200 numbers higher than the element numbers of FIG. 3.

Figure 8:
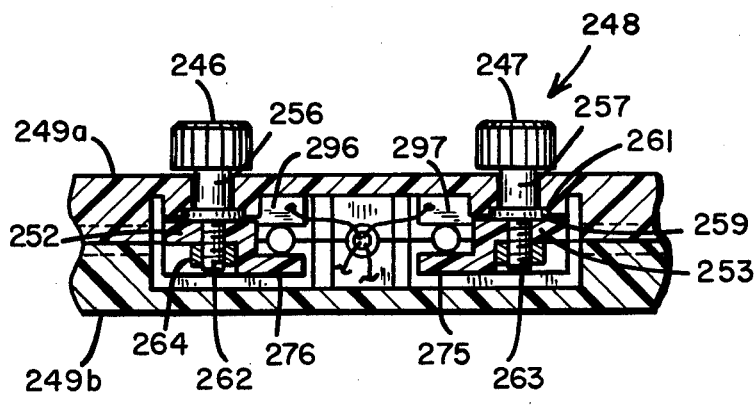
FIG. 8 is a cross-sectional view of the lead connector of FIG. 6 taken along the lines 8—8 of FIG. 6.

FIG. 8 is a cross-sectional view of FIG. 6 taken along the lines 8—8 shows a second clamping block 253 that is associated with the clamping knob 247. Assembly is identical to the corresponding elements associated with the knob 246. The corresponding element numbers for this clamping block and shaft assembly are the same as those for the clamping block 252 and shaft assembly 248 described in connection with FIG. 7 except that they are one number higher than the corresponding element numbers of FIG. 7. The operation and construction of the clamping arrangements of FIGS. 7 and 8 therefore follow the description previously contained herein with regard to the clamping provisions of FIG. 3, taking into account the aforementioned element number changes. FIG. 5 is an exploded view of the connector of FIGS. 6-8 in which the corresponding element numbers referred to in FIGS. 7 and 8 are employed. With this connector embodiment, however, both atrial and ventricular leads may be connected through the cable to the pulse generator. For example, if the left-hand section of the lead connector were employed to clamp the atrial lead, then the right-hand section could be employed to clamp the ventricle lead. With the connector of FIGS. 6-8 it is not necessary for both the atrial and ventricular leads to be of the same type. Thus, they may both be bifurcated leads, they may both be in-line leads or alternately, one of them may be a bifurcated lead while the other is an in-line lead. This universality is an important feature of the lead connector of the present invention. The cable 212 may be inserted into the lead connector 210 through the opening formed by the notch 278 and a similar notch in the upper housing half 249 (not shown) with strain relief in the embodiment of FIG. 9 again being provided by the walls 286, 288. A bifurcated lead may be inserted into the housing through the channels 305, 307 so as to make contact respectively with the electrodes 294, 296. Alternately, an in-line bipolar lead may make connection with the electrodes 294, 296 by insertion through the rear of the housing in the channel 309 or through the front of the housing in the channel 311. Unlike the connector of FIGS. 1-5, however, there are no stop walls which assist in aligning the lead electrodes with the connector electrodes. The projection 302 on the clamping block 252 in the connector FIGS. 6-9 fits into a curved wall section 313 which corresponds to the shape of the projection 302 to prevent the clamping means 252 from rotating when it is drawn towards the electrodes 294, 296. The clamping block 252 may rock in the manner described with reference to the clamping block 52 of FIG. 3 so that lead electrodes of different diameters may be clamped between the arms 274, 276 and the electrodes 294, 296 in the connector.

In a similar manner, if an atrial lead is connected on the left-hand section of the connector of the ventricular lead may be connected to the electrodes 295, 297 on the right-hand section of the connector. This is done by passing bifurcated leads through the channels 315, 317 or by passing in-line leads through the lead channel 319 in the front of the connector, or the lead connector 321 in the rear of the connector. When these leads are inserted into the housing, they are correspondingly clamped by the arms 277, 275 of the clamping block 253 against the electrodes 295, 297. The wires 290, 292 will thus be associated with the atrial pacing lead while the wires 291, 293 will be associated with the ventricular lead, in this instance.

Figure 9:
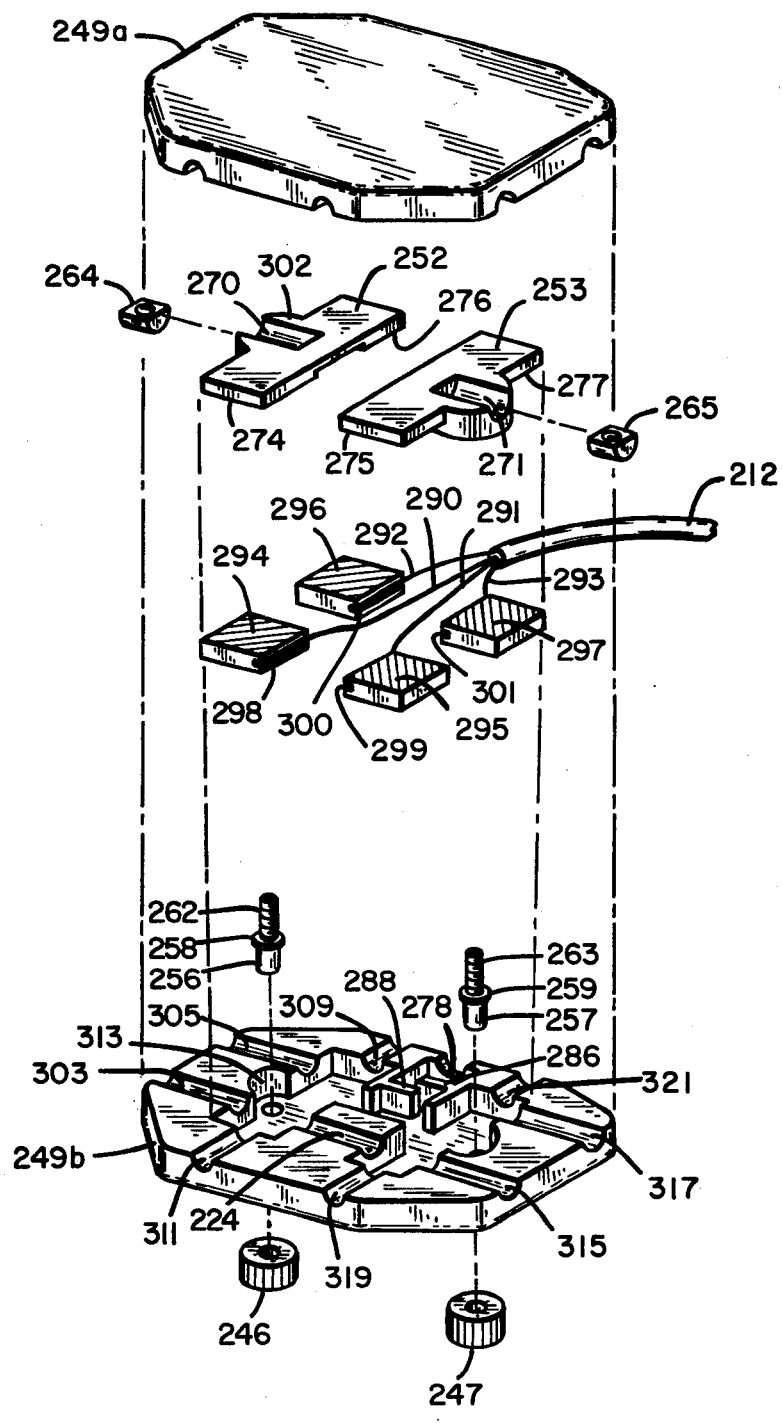
FIG. 9 is an exploded view of a lead connector that corresponds to the lead connector of FIG. 6.

Although the invention has been described wherein the atrial and ventricular connecting leads are connected in separate sides of the connector, it is possible with the connector constructed in the manner illustrated in FIG. 9 to make various other combinations of lead connections involving a bipolar or unipolar leads.

For example, a unipolar lead may pass through the passageway 315 and over the channel 224 for connection to the electrode 294. In a similar manner, a lead passing through the channel 307 and across the channel 224 may be connected to the electrode 295. A second unipolar lead could then be connected either to the electrode 296 through the channel 305 or to the electrode 297 and through the channel 305 or to the electrode 297 and through the channel 317. Thus, although the connector of FIGS. 6-9 is an extremely simple construction, it has a high degree of adaptability since it can connect different types of leads, and even leads of different diameters, to a cardiac pacing pulse generator in a variety of connection configurations.

What is claimed is:

1. A lead connector for connecting pacing leads to a pulse generator comprising:
    a housing having at least one inlet opening for an in-line electrode lead and at least one pair of spaced inlet openings for a bifurcated lead;
    at least one pair of connector electrodes secured in said housing and positioned to contact the electrodes of said leads when they are inserted into said inlet opening;
    at least one clamping means wherein each clamping means is associated with a pair of connector electrodes, and comprises a threaded shaft having a free end that extends into said housing, a clamping block through which said free end of said threaded shaft protrudes and a securing means which is threaded onto said free end of the said threaded shaft, wherein said securing means has a curved surface and said clamping block comprises a mating curved surface for the curved surface of said securing means, which receives and prevents said securing means from rotating independently of said clamping block and, each of said clamping blocks has a restricted passageway that allows said threaded shaft to pass therethrough so that said clamping blocks may rock to a limited extent relative to said threaded shaft by sliding of its mating curved surface on the curved surface of its associated securing means to a position limited by the diameter of said passageway, and said clamping blocks are driven toward a pair of associated connector electrodes, so as to clamp the inserted lead electrodes between integrating formed surfaces on said clamping block which extend outwardly of said threaded shaft, and the associated pair of connector electrodes, upon rotation of its associated threaded shaft in one direction, and said clamping blocks are driven away from said associated pair of connector electrodes, upon rotation of said associated threaded shaft in the opposite direction;
    said housing having housing top means formed thereon which engage said clamping means and prevent said clamping means from rotating after a limited amount of rotation has occurred.

2. A lead connector as claimed in claim 1 wherein said housing has integral walls formed thereon which stop the passage of each of said leads into said housing at a proper location for placing the electrodes of said leads adjacent the appropriate connector electrodes.

3. A lead connector as claimed in claim 1 wherein said housing comprises two separate inlet openings, one of which is for an in-line atrial pacing lead and the other of which is for an in-line ventricular pacing lead, and two pairs of spaced inlet openings, one pair of which is for a bifurcated atrial pacing lead and the other pair of which is for a bifurcated ventricular pacing lead, said connector electrodes comprise an atrial pair of connector electrodes and a ventricular pair of connector electrodes and said connector comprises an atrial lead clamping means and a ventricular lead clamping means for respectively clamping said electrodes of said atrial leads against said atrial connector electrodes and said electrodes of said ventricular leads against said ventricular connector electrodes upon rotation of the associated threaded shaft in the appropriate direction.

4. A lead connector as claimed in claim 3 wherein said housing has integral walls formed thereon which stop the passage of each of said leads into said housing at a proper location for placing the electrodes of said leads adjacent the appropriate connector electrodes.

* * * * *